United States Patent [19]
Sutherland et al.

[11] Patent Number: 5,985,619
[45] Date of Patent: *Nov. 16, 1999

[54] USE OF EXONUCLEASE AND/OR GLYCOSYLASE AS SUPPLEMENTS TO ANTI-POLYMERASE ANTIBODY TO INCREASE SPECIFICITY IN POLYMERASE CHAIN REACTION

[75] Inventors: John William Henderson Sutherland; David Robert Patterson, both of Rochester, N.Y.

[73] Assignee: Clinical Diagnostic Systems, Inc., Rochester, N.Y.

[ * ] Notice: This patent issued on a continued prosecution application filed under 37 CFR 1.53(d), and is subject to the twenty year patent term provisions of 35 U.S.C. 154(a)(2).

[21] Appl. No.: 08/643,282

[22] Filed: May 8, 1996

Related U.S. Application Data

[63] Continuation of application No. 08/385,019, Feb. 7, 1995, abandoned.

[51] Int. Cl.$^6$ .............. C12P 19/34; C12Q 1/68; C07H 21/02
[52] U.S. Cl. .............. 435/91.2; 435/6; 536/24.3; 536/24.31; 536/24.32; 536/24.33
[58] Field of Search .............. 435/6, 91.2; 536/24.3, 536/24.31, 24.32, 24.33

[56] References Cited

U.S. PATENT DOCUMENTS

| | | | |
|---|---|---|---|
| 5,273,890 | 12/1993 | Steinman | 435/91.2 |
| 5,418,149 | 5/1995 | Gelfand | 435/91.2 |
| 5,605,796 | 2/1997 | Chen et al. | 435/6 |

FOREIGN PATENT DOCUMENTS

| | | |
|---|---|---|
| 487 218 A1 | 5/1992 | European Pat. Off. . |
| 585 660 A3 | 3/1994 | European Pat. Off. . |
| 592 035 A2 | 4/1994 | European Pat. Off. . |
| WO 92/01814 | 2/1992 | WIPO . |

OTHER PUBLICATIONS

Sharkey, et al.: "Antibodies as Thermolabile Switches: High Temperature Triggering for the Polymerase Chain Reaction", *Biotechnology*, vol. 12, May 1994, New York, U.S. pp. 506–509.

Longo, et al.: "Use of Uracil DNA Glycosylase to Control Carry–Over Contamination in Polymerase Chain Reactions", *Gene,* vol. 93, No. 1, Jan. 1990, Amsterdam, NL pp. 125–128.

Li et al.: "Eliminating Primers from Completed Polymerase Chain Reactions with Exonuclease VII", *Nucleic Acids Research,* vol. 19, No. 11, Jun. 11, 1991, Oxford, GB, pp. 3139–3141.

Zhu, et al.: "The Use of Exonuclease III for Polymerase Chain Reaction Sterilization", *Nucleic Acids Research,* vol. 19, No. 9, May 11, 1991, Oxford, GB, p. 2511.

Findlay et al, (1993), "Automated closed–vessel system for in vitro diagnostics based on polymerase chain reaction", Clin. Chem. 39(9):1927–1933.

Longo et al, (1990), "Use of uracil DNA glycosylase to control carryover contamination in polymerase chain reactions" Gene 93:124–128.

Stratagene catalog, (1988), p. 39.

Hanke et al, (May 1994), "Direct DNA sequencing of PCR–amplified vector inserts following enzymatic degradation of primer and dNTPs" Biotechniques 17(5):858–860.

Ott et al, (1987), "Protection of oligonucleotide primers against degradation by DNA polymerase I", Biochemistry 26:8237–8241.

Scalice et al, (1994), "Monoclonal antibodies prepared against the DNA polymerase from *Thermus aquaticus* are potent inhibitors of enzyme activity", J. Imm. Meth. 172:147–163.

Kellog et al, (1994), "TaqStart antibody™: Hot Start PCR facilitated by a neutralizing monoclonal antibody directed against Taq DNA polymerase", Biotechniques 16(6):1134–1137.

Kox et al, (Mar. 1994), "A more reliable PCR for detection of *Mycobacterium tuberculosis* in clinical samples", J. Clin. Microbiol. 32(3):672–678.

Sharkey et al (May 1994), "Antibodies as thermolabile switches: high temperature in clinical samples", J. Clin. Microbiol. 32(3):672–678.

Scalice et al, (1993), "The use of Mg + 2 encapsulation or TAQ DNA polymerase inhibiting antibodies to prevent o–cycle artifacts in the polymerase chain reaction", Clin. Chem. 39(6):1180.

Stratagene catalog, p. 196, 1995.

Promega catalog, p. 55, 1993.

*Primary Examiner*—Jeffrey Fredman

[57] ABSTRACT

The present invention provides admixtures and methods for PCR amplification of a target nucleic acid in which amplification efficiency is increased by including an antibody specific for a polymerization agent and at least one of an exonuclease and a glycosylase in the PCR reaction mix. Kits for amplification of a target nucleic acid are also provided.

26 Claims, No Drawings

USE OF EXONUCLEASE AND/OR GLYCOSYLASE AS SUPPLEMENTS TO ANTI-POLYMERASE ANTIBODY TO INCREASE SPECIFICITY IN POLYMERASE CHAIN REACTION

This is a continuation of application Ser. No. 08/385,019, filed Feb. 7, 1995 now abandoned.

FIELD OF THE INVENTION

Polymerase chain reaction (PCR) allows amplification and detection of small quantities of a target nucleic acid. Practical limitations of PCR include the production and amplification of non-specific side products, in particular primer-dimers and higher order oligomers such as primer-tetramers. The present invention provides compositions and methods to overcome such limitations and thereby to increase the accuracy and sensitivity of PCR.

BACKGROUND OF THE INVENTION

The technology of PCR permits amplification and subsequent detection of minute quantities of a target nucleic acid. Details of PCR are well described in the art, including, for example, U.S. Pat. Nos. 4,683,195 to Mullis et al., 4,683,202 to Mullis and 4,965,188 to Mullis et al. Generally, oligonucleotide primers are annealed to the denatured strands of a target nucleic acid, and primer extension products are formed by the polymerization of deoxynucleoside triphosphates by a polymerase. A typical PCR method involves repetitive cycles of template nucleic acid denaturation, primer annealing and extension of the annealed primers by the action of a thermostable polymerase. The process results in exponential amplification of the target nucleic acid, and thus allows the detection of targets existing in very low concentrations in a sample.

PCR is widely used in a variety of applications, including biotechnological research, clinical diagnostics and forensics. However, the methodology is subject to practical limitations that result in less than optimal efficiency and specificity. In particular, before the first cycle of a PCR experiment (i.e. at "zero cycle"), the reagents for amplification are typically mixed and stored at room temperature or lower. Because thermostable polymerases, for example, *Thermus aquaticus* (Taq) polymerase, have residual activity even at 0° C., relatively large quantities of non-specific products can be formed by low stringency priming and replication. The non-specific products, known as zero cycle artifacts, include primer-dimers formed by ligation of primers having homology at their 3' ends. Because of the micromolar concentrations of primers used in PCR relative to the often minute concentrations of target, the formation of primer-dimers is predominant. Primer-dimers are thus particularly pervasive zero-cycle artifacts. Other primer based amplification systems, such as solid phase amplification, similarly suffer from primer-dimer artifacts.

The formation of zero-cycle artifacts during amplification has practical consequences. Reagents, including primers and deoxyribonucleosides, may be depleted, and the non-specific side products act as competitive inhibitors with respect to the target for the polymerase and other limiting components of the reaction. Consequently, amplification efficiency may be decreased and assay precision degraded. Any decrease in amplification efficiency may adversely effect the assay detection limit, and thus potentially cause false negative results. As demonstrated in accordance with the present invention, primer-dimer formation can reduce efficiency of target amplification to such a degree that the amplified product is not detectable on a stained gel. Such a result would clearly be undesirable in tests for pathogenic organisms, such as HIV.

Specificity is particularly important in homogeneous PCR reactions. See, e.g., EPA 487218 to Mitoma; EPA 512334 to Higuchi. In the homogeneous assays, PCR amplification and detection are coupled by contacting the reaction mixture, during or after amplification, with a fluorescent pigment that undergoes a detectable change in fluorescence upon reaction with a double-stranded nucleic acid. For example, when PCR is conducted in the presence of ethidium bromide, the production of double-stranded DNA is correlated with an increase in fluorescence as free ethidium bromide becomes intercalated into double-stranded DNA. Generally, amplification and detection are carried out in the same vessel. Changes in fluorescence are detected spectrophotometrically, and thus detection requires neither separation of PCR products nor hybridization. Because detection is based upon formation of double-stranded DNA generally, and fails to discriminate between target DNA and non-specific products, the formation of double-stranded artifacts such as primer-dimers is fatal to the specificity of the homogeneous assay.

Various strategies have been developed to increase PCR specificity. Theoretically, primer-dimer artifacts can be avoided by selecting primers with no 3'-homology. In practice, however, some 3' homology may be unavoidable, particularly in applications that require mixtures of primers. Coamplification of numerous strains or alleles of a target are typical applications that require a large number of primers.

Specificity can also be improved by increasing stringency, for example, by increasing the annealing temperature or incorporating denaturing solvents. However, increasing stringency may lead to false negative results because the assay's ability to detect mutated forms of the target, which may have been amplified at lower stringency, is reduced.

In another method of reducing zero-cycle artifacts, the so-called "hot start" method of PCR, the reaction is started by the addition of polymerase to hot reagent mixtures. (See, e.g., Erlich et al. (1991) *Science* 252:1643.) Primer-dimers are reduced since the reactive intermediates formed by cross-reaction of primers are thermally unstable. However, this method does not provide the convenience of room temperature preparation, and is subject to complications caused by timing errors resulting from manual addition of polymerase to multiple (typically 96) PCR tubes.

Thermolabile physical barriers, such as paraffin beads or overlays, have been used to physically separate one or more PCR components from the others until temperatures suitable for high stringency priming are reached (See, e.g., Hébert et al. (1993) *Molecular and Cellular Probes* 7:249). However, these methods are generally inconvenient and require considerable manual dexterity.

Thermally labile antibodies to Taq polymerase have been used to inhibit Taq polymerase at low temperatures in an attempt to limit zero cycle artifacts. (See, e.g., Sharkey et al. (1994) *Bio/Technology* 12:506; U.S. Pat. No. 5,338,671 to Scalice et al.) When the temperature is elevated in the PCR thermal cycling, the antibodies are thermally denatured and active polymerase is released. However, even avid antibodies do not completely inhibit polymerase activity. For example, one micromolar antibody having affinity of $10^{10} M^{-1}$ acting on polymerase at a concentration of 10 nanomolar in a volume of 100 microliters would leave 60 million molecules of free active polymerase at equilibrium.

Since primer levels used in PCR are relatively large, sizable numbers of primer-dimer intermediates can nonetheless be formed and amplified. As a result and as demonstrated in accordance with the present invention, anti-Taq antibody alone may be insufficient to suppress primer-dimer formation, especially in cases in which the primers have substantial 3' homology or in which the homology consists of strong G—C bonds.

Enzymes capable of digesting primer-dimer intermediates have also been disclosed for use in side product suppression. Zhu et al. (1991) *Nucleic Acids Res.* 19:251) report the use of exonuclease III (Exo III) for "pre-PCR sterilization" to reduce amplicon and primer-dimer carry over. However, since Exo III catalyzes the sequential cleavage of 5' mononucleotides from the 3' hydroxyl end of duplex DNA, it may also attack target DNA. Further Zhu et al. report that Exo III does not degrade single-stranded DNA, and thus single-stranded primer-dimers could be expected to escape Exo III treatment and thereby be susceptible to amplification. Muralidhar et al. (1992) *Gene* 117:107 report the use of T7 exonuclease to reduce amplification of carry over PCR product molecules. The contaminating PCR molecules are preferentially inactivated due to their symmetric geometry relative to genomic target molecules. Muralidhar et al. fail to reduce primer-dimer products, and note that the geometry of primer-dimers has not been established.

The enzyme uracil-N-glycosylase (UNG) has also been used in a preamplification step to cleave products made during the zero cycle at incorporated uracil residues. (See, e.g., Longo et al. (1990) *Gene* 93:125; Espy et al. (1993) *J. Clin. Microbiol.* 31:2361.) Deoxyuridine triphosphate (dUTP) is substituted for deoxythymidine triphosphate (dTTP) in the PCR and thus PCR products can be distinguished from template DNA. The enzyme UNG is included in the premix, and catalyzes the excision of uracil from single or double-stranded DNA present in the reaction prior to the first PCR cycle. The resulting abasic polynucleotides are susceptible to hydrolysis and cannot function as templates during PCR. While UNG is reportedly inactivated by thermal denaturation, residual activity may degrade amplification products synthesized during PCR. Further, Longo et al. compared the relative amount of amplification product in the presence and absence of UNG treatment, and reported a reduction in the intensity of the amplified target in reactions with UNG treatment. Thus UNG treatment would not be expected to solve the problem of inefficiency of product amplification.

Epsy et al. report that the efficiency of UNG in inactivating amplified DNA is dependent upon the length of the DNA. In particular, UNG was ineffective in inactivating PCR amplicons of less than 100 base pairs. Accordingly, UNG fails to inactivate primer-dimers.

As demonstrated in accordance with the present invention, neither Exo III nor UNG is particularly effective for suppression of primer-dimers and improved amplification efficiency. Further, as discussed hereinabove, the prior art methods of suppressing zero cycle artifacts suffer from practical deficiencies. Accordingly, there is a need in the art for practical and effective methods of suppressing zero cycle artifacts and thus increasing PCR efficiency and specificity.

SUMMARY OF THE INVENTION

The present invention is directed to a method for the amplification of a target nucleic acid comprising contacting a sample suspected of containing a target nucleic acid with at least two oligonucleotide primers that are sufficiently complementary to conserved regions of the target nucleic acid to hybridize thereto, at least four different nucleoside triphosphates, a thermostable polymerization agent, at least one antibody specific to the polymerization agent, and at least one of an exonuclease and a glycosylase to form a reaction admixture; heating said reaction admixture to denature the antibody, the exonuclease and/or the glycosylase, and to separate the strands of the target nucleic acid, and forming primer extension products. In those embodiments utilizing a glycosylase, one of the nucleoside triphosphates is one which, when incorporated into DNA, is specifically cleaved by the glycosylase.

In another embodiment, the present invention provides a method for reducing formation of non-specific nucleic acids and increasing efficiency of amplification of a desired target in a PCR amplification method which comprises: contacting the sample to be tested with reagents for amplification including a polymerization agent, at least one antibody specific to the polymerization agent, and at least one of an exonuclease and a glycosylase; heating said sample to denature the antibody, the exonuclease and/or the glycosylase and to separate the strands of the target nucleic acid; and amplifying said target nucleic acid.

The present invention further provides a kit for amplification of a nucleic acid comprising a first container adapted to contain a thermostable polymerization agent, a second container adapted to contain an antibody specific to the polymerization agent, and a third container adapted to contain an exonuclease. In another embodiment, the kit further comprises a fourth container adapted to contain a glycosylase. Additional containers can be provided to the kit to incorporate additional antibodies and/or other PCR reagents as desired.

The present invention also comprises a kit for amplification of a nucleic acid comprising a first container adapted to contain a thermostable polymerization agent, a second container adapted to contain an antibody specific is the polymerization agent, and a third container adapted to contain a glycosylase. In another embodiment, the kits of the present invention further contain reagents for PCR including nucleoside triphosphates, primers, buffers and additional antibodies.

A further aspect of the present invention provides an admixture composition useful for PCR amplification and in particular for reducing formation of non-specific nucleic acids during PCR. This admixture comprises at least one antibody to the thermostable polymerization agent employed in the PCR process and at least one of an exonuclease and a glycosylase. The admixture composition may also include at least four different nucleoside triphosphates, a polymerization agent, at least two oligonucleotide primers and other PCR reagents such as buffers and the like.

DETAILED DESCRIPTION OF THE INVENTION

The present invention provides a method for the amplification of a target nucleic acid whereby non-specific amplification of nucleic acids, also known as zero-cycle artifacts, is reduced relative to conventional methods of PCR. In particular, the formation of primer-dimers is reduced and thus efficiency of amplification of target nucleic acids is increased by including in the PCR reaction mix an antibody specific to the thermostable polymerization agent and at least one of an exonuclease and a glycosylase.

The principles of PCR and the conditions for amplification and detection of target nucleic acids are well known in the art and may be found in numerous references known to the skilled artisan, including, for example, U.S. Pat. Nos. 4,683,195 to Mullis et al., 4,683,202 to Mullis et al. and 4,965,188 to Mullis et al. Briefly, a sample suspected of containing a target nucleic acid is heated to denature double-stranded nucleic acid in the presence of two oligonucleotide primers that are complementary to target sequences flanking the region to be amplified. The primers anneal to the separated target strands and are extended from each 3' hydroxyl end by a polymerizing agent such as a thermostable polymerase. Double-stranded or single-stranded DNA can be amplified by PCR. RNA can also serve as a target by reverse transcribing RNA into cDNA. The steps of denaturation, primer annealing and DNA synthesis are carried out at discrete temperatures, and repeated cycles result in exponential accumulation of the target nucleic acid. The PCR vessel is generally a stoppered plastic vessel or a cuvette or pouch as described in U.S. Pat. No. 5,229,297. Reagents for PCR amplification are typically mixed in a single vessel, and generally include primers, nucleoside triphosphates (generally dATP, dCTP, dGTP and dTTP or dUTP), thermostable DNA polymerase, magnesium containing buffer, and target nucleic acid. Reagents and conditions for PCR are well-known to one of ordinary skill in the art, and can be found, for example, in Guatelli et al. (1989) *Clin. Microbiol. Rev.* 2:217. For amplification of RNA targets, a reverse transcriptase may be utilized in addition to or in lieu of the thermostable DNA polymerase. Thermostable reverse transcriptase are particularly useful, as are thermostable DNA polymerases having reverse transcriptase activity. Methods for PCR amplification of RNA targets are known to one of ordinary skill in the art and described, for example, in U.S. Pat. Nos. 5,176,995, 5,310,652 and 5,322,770.

The present invention provides a modification of known methods of PCR in order to improve the efficiency of amplification of a target nucleic acid. In particular, the methods of the present invention reduce the formation of zero cycle artifacts including primer-dimers with a concurrent increase in the efficiency of amplification of target DNA. Primer-dimers may be double-stranded PCR products consisting of the two primers and their complementary sequence. Additional bases may be inserted between the primers. (Erlich et al., (1991) *Science* 252:1643). Denaturation of these species results in single-stranded artifacts also included by the term primer-dimer. Primer-dimer formation is particularly favored when primers have homology at the 3' ends, and may result in reduced amplification efficiency to such a degree that amplified target cannot be detected. While various methods have been proposed in the art to reduce primer-dimer formation and to increase amplification efficiency, it has been shown in accordance with the present invention that the prior art methods of use of anti-Taq antibody or Exo III or UNG individually are incapable of detectably reducing primer-dimers or increasing efficiency in many situations.

The method of the present invention thus allows improved efficiency of amplification, reduction in false negative results, and also allows the practitioner more flexibility in choosing primer sequences, since 3' homology of primers need not be avoided.

In the first instance, the present invention provides an admixture useful for PCR amplification and particularly for reducing formation of non-specific nucleic acids during PCR. This admixture includes at least one antibody to the thermostable polymerization agent employed in the PCR process and at least one of an exonuclease and a glycosylase. The admixture preferably includes an exonuclease and a glycosylase and at least one antibody. The admixture also includes other PCR reagents such as nucleoside triphosphates, polymerization agents, primers, buffers and the like.

It has been surprisingly discovered in accordance with the present invention that non-specific nucleic acids are reduced and efficiency of amplification of target nucleic acids is increased by contacting the sample containing the target nucleic acid and reagents for PCR with an antibody specific for the PCR polymerization agent and an exonuclease; or an antibody specific for the PCR polymerization agent and a glycosylase; or an antibody specific for the PCR polymerization agent, an exonuclease and a glycosylase. More than one antibody specific for the PCR polymerization agent can be employed.

The method of the present invention thus allows improved efficiency of amplification and reduction in false negative results, and further allows the practitioner more flexibility in choosing primer sequences, since 3' homology or primers need not be avoided.

The method of the present invention is particularly useful in PCR amplification and detection methods known in the art as homogeneous assays or homogeneous detection systems. Such systems are well-known in the art and are described, for example, in published European Patent Applications 91310062.4 (487218) and 92106989.4 (512334). In the homogeneous systems, detection of amplified DNA is based upon changes in fluorescence induced by binding of a fluorescent compound to double-stranded DNA. Because detection is based upon formation of double-stranded DNA generally, and fails to distinguish between target DNA and non-specific products, the formation of double-stranded artifacts such as primer-dimers is detrimental to the specificity of the homogeneous assay. In accordance with the present invention, primer-dimers are reduced and thus the specificity of the homogeneous detection method is increased.

The reagents required for PCR are known to the ordinarily skilled artisan, and generally include at least two oligonucleotide primers that are sufficiently complementary to conserved regions of the target nucleic acid to hybridize thereto, four different nucleoside triphosphates, a thermostable polymerization agent and any requisite cofactors for the polymerization agent. Preferred nucleoside triphosphates are the deoxyribonucleoside triphosphates dATP, dCTP, dGTP and dTTP collectively termed dNTPs. In methods of the present invention utilizing UNG, dUTP is substituted for dTTP. Nucleoside triphosphates are commercially available.

Primers include naturally occurring or synthetically produced oligonucleotides capable of annealing to the target nucleic acid and acting as the point of initiation of nucleic acid synthesis under appropriate conditions, i.e., in the presence of nucleoside triphosphates, a polymerization agent, suitable temperature, pH and buffer. The primers have sequences sufficiently complementary to the target nucleic acid to hybridize thereto, and are of sufficient length, typically from 10–60 nucleotides, to prime the synthesis of extension products in the presence of a polymerization agent. Primers may be produced synthetically by automated synthesis by methods well known to one of ordinary skill in the art.

Design considerations for primers are well known in the art. Primers are selected to be substantially complementary to the sequences of the strands of the specific nucleic acid to be amplified, such that the extension product synthesized from one primer, when separated from its complement, can serve as a template for the extension product of the other primer. Preferably, the primers have exact complementarity with the target strand.

Polymerization agents are compounds that function to accomplish the synthesis of the primer extension products. The polymerization agents are thermostable, i.e., not permanently inactivated when heated for brief periods to temperatures typically used in PCR for denaturation of DNA strands, e.g., 93–95° C., and are preferentially active at high temperatures. In a preferred embodiment the polymerization agent is a thermostable DNA polymerase, including, for example, DNA polymerase obtained thermophilic bacteria such as, *Thermococcus litoralis, Bacillus stearothermophilus, Methanothermus fervidus, Thermus aquaticus, T. filiformis, T. flavus, T. lacteus, T. rubens, T. ruber* and *T. thermophilus*; or from thermophilic archaebacteria such as *Desulfurococcus mobilis, Methanobacterium thermoautotrophilcum, Sulfolobus solfataricus, S. acidocaldarius* and *Thermoplasma acidophilum*. In a most preferred embodiment, the polymerization agent is Thermus aquaticus (Taq) polymerase, *T. thermophilus* (Tth) polymerase or Thermococcus litoralis polymerase. Thermostable reverse transcriptase and DNA polymerases having reverse transcriptase activity are also contemplated as polymerization agents.

The thermostable polymerases may be obtained commercially or by methods known in the art. In particular, Taq polymerase is available commercially in recombinant and native form (Perkin Elmer-Cetus) or can be produced by the method described by Lawyer et al. (1989) *J. Biol. Chem.* 264:6427 or in U.S. Pat. No. 4,889,818. Tth polymerase is commercially available from-Finnzyme Co., Finland and from Toyobo Co., Japan. Thermococcus litoralis is commercially available from New England Biolabs and can be produced by the method described in U.S. Pat. No. 5,322,785.

Antibodies specific for the thermostable polymerization agents can be produced by methods known to one of ordinary skill in the art. In accordance with the present invention, the term antibodies includes monoclonal and polyclonal antibodies produced by conventional methodologies, recombinantly produced antibodies, and chemically or recombinantly produced fragments of antibodies, such as Fab fragments. In a preferred embodiment, the antibodies are monoclonal.

Antibodies can be obtained by methods known to the ordinarily skilled artisan, and found, for example, in Harlowe et al. (1988) *Antibodies: A Laboratory Manual*, Cold Spring Harbor, N.Y. For example, polyclonal antibodies can be prepared by immunizing a suitable host mammal with a polymerization agent such as a DNA polymerase and a suitable adjuvant (for example, Freund's complete adjuvant). Booster injections can be given at various intervals to increase titer. Serum samples are generally collected at certain time intervals and tested for specificity for the DNA polymerization agent of interest, for example, by ELISA or immunoblotting. Desired sera of sufficient titer are generally purified using conventional means such as ion exchange and affinity chromatography (for example, using Protein A or Protein G matrices).

Monoclonal antibodies are conveniently prepared from the immune cells of mice or rats immunized with the polymerization agent using conventional procedures. For example, antibody secreting cells of the host animal are isolated from lymphoid tissue (such as the spleen) and fused with myeloma cells (for example, SP2/0-Ag14 murine myeloma cells) in the presence of polyethylene glycol, diluted into selective media and plated in multiwell tissue culture dishes. About 7–14 days later, the hybridoma cells which secrete the desired antibodies are harvested for use or frozen in storage. The culture supernatants can also be tested for the presence of the desired antibodies. To produce a sufficient amount of antibody, the hybridoma cells can be grown in static culture, hollow fiber bioreactors or used to produce ascitic tumors in mice. Purification can be carried out as described for polyclonal antibodies.

Similarly, monoclonal antibodies against Taq polymerase-can be obtained as described in U.S. Pat. No. 5,338,671.

In a preferred embodiment of the present invention, the antibody is a monoclonal antibody against Taq polymerase, Tth polymerase, or Thermococcus litoralis polymerase. In a more preferred embodiment, the antibody is a monoclonal antibody against Taq polymerase. Monoclonal antibodies against Taq polymerase are known in the art and described, for example, in U.S. Pat. No. 5,338,671. In a preferred embodiment the monoclonal antibodies against Taq polymerase are TP4-9.2 and TP1-12.2, obtainable from hybridomas deposited with the American Type Collection, 12301 Parklawn Drive, Rockville, Md., 20853 and designated by ATCC Accession Numbers HB11807 and HB11127, respectively. Preferred antibodies have an association constant for the polymerase of at least about $1 \times 10^7$ $M^{-1}$. In accordance with the present invention, antibodies defined as specific for polymerization agent are those antibodies that are capable of inhibiting the enzymatic activity of the polymerization agent at temperatures from about 20–40° C. The antibodies of the invention are inactivated by elevated temperatures used during PCR thermal cycling. The ability of the antibodies to inhibit enzymatic activity of the polymerase can be determined by assays known to one of ordinary skill in the art, as described, for example, by Sharkey et al. (1994) *BioTechnology* 12:506. For example, standard assays for the enzymatic activity of DNA polymerases may be based upon the ability of the polymerase to incorporate $^3$H-dNTP in single strand gaps made in DNA. The ability of an antibody to inhibit polymerase activity is determined by preincubating antibody with the polymerase and then conducting the standard polymerase assay. Antibodies capable of significantly decreasing polymerase activity in such an assay are useful in the present invention. Similar assays may be used to determine that the desired antibodies are inactivated by heat. Briefly, the assay for the ability of the antibody to inhibit the polymerase is modified by raising to the desired temperature, followed by cooling and assaying for polymerase activity. The desired antibodies in accordance with the present invention are inactivated by temperatures of 85–95° C., thus releasing active polymerase.

The exonucleases used in accordance with the present invention are commercially available or can be obtained by methods known in the art and include, for example, exonuclease III (Exo III), exonuclease I, λ exonuclease, T7 exonuclease, ribonuclease II, polynucleotide phosphorylase and BAL 31 nuclease. Exonucleases are known to the ordinarily skilled artisan, and are described, for example, by Fasman, ed. (1989) *Practical Handbook of Biochemistry and Molecular Biology*, CRC Press, BocaRaton, Fla. Both 5' and 3' exonucleases are contemplated in accordance with the present invention, as are exonucleases that digest single-stranded DNA, double-stranded DNA or both. Exonucleases that preferentially attack double-stranded DNA are particularly preferred. In a preferred embodiment, the exonuclease is Exo III, λ exonuclease or exonuclease I. Exo III is particularly preferred. Inactivation of the exonuclease at 95°

C. prevents further exonuclease activity during thermal cycling. Accordingly, the exonuclease must be inactive at 95° C.

The glycosylases useful in the present invention are those that specifically cleave unconventional bases, i.e., bases other than A, G, C or T in DNA and A, G, C and U in RNA. In embodiments of the present invention utilizing a glycosylase, the appropriate deoxyribonucleoside triphosphate for which the glycosylase is specific is substituted for the corresponding conventional dNTP. Glycosylases that specifically cleave unconventional bases such as N-7 methylguanine, 3-methyladenosine, uracil and hypoxanthine are known to one of ordinary skill in the art and described, for example, in PCT/US91/05210 to Sninsky St A. Preferred glycosylases include uracil N-glycosylase (UNG), hypoxanthine-DNA glycosylase, and 3-methyadenine-DNA glycosylases I and II. The most preferred glycosylase in accordance with the present invention is UNG. UNG is commercially available (Perkin-Elmer). UNG catalyzes the excision of uracil from single or double-stranded DNA. In embodiments of the present invention utilizing UNG, the deoxyribonucleoside triphosphate dUTP is substituted for dTTP so that dUTP is incorporated into amplification products. Because UNG is inactivated by temperatures used in thermal cycling, UNG attacks only uracil containing DNA that is produced prior to thermal cycling, i.e., at zero cycle. The abasic polynucleotides resulting from UNG cleavage cannot function as PCR templates. (Longo et al. (1990) *Gene* 93:125).

The present invention provides a method for the amplification of a target nucleic acid, and optionally, the subsequent detection of the nucleic acid, in a sample suspected of containing the target nucleic acid. The sample may be any sample suspected of containing a target nucleic acid, including, for example, a tissue sample, blood, hair, body fluid, bacteria, virus, fungus, bacterial infected cell, virally infected cell, and so on. The target nucleic acid may be DNA or RNA. A sufficient number of bases at both ends of the sequence to be amplified must be known in order to design primers capable of hybridizing to the different strands of the target nucleic acid at suitable positions for PCR amplification. The target nucleic acid may be extracted or partially extracted from the tissue sample prior to PCR, for example, by removing proteins or cellular material from the sample. Methods for extracting nucleic acids from samples are known to one of ordinary skill in the art and may be found, for example, in Sambrook et al. (1989) *Molecular Cloning: A Laboratory Manual*, Cold Spring Harbor Laboratory Press, Cold Spring Harbor, N.Y. and Saiki et al. (1985) *BioTechnology* 3:1008.

In the method of amplification of the present invention, the sample or a preparation of nucleic acids extracted from the sample is contacted with the reagents typically used for PCR, including at least two oligonucleotide primers, four different nucleoside triphosphates, a thermostable polymerization agent, and an appropriate buffer, and further with at least one antibody specific for the polymerization agent and at least one of an exonuclease and a glycosylase to provide a PCR reaction mixture. In a preferred embodiment, both exonuclease and glycosylase are included.

The conventional PCR reagents, including primers, nucleoside triphosphates, polymerization agent, and appropriate buffer are utilized at concentrations generally appropriate for PCR and known to one of ordinary skill in the art. In a preferred embodiment, the nucleoside triphosphates are dATP, dCTP, dGTP and dTTP. In methods utilizing a glycosylase, dUTP is substituted for dTTP and magnesium concentration in the buffer is lowered, for example, to about 5 mM in 10×PCR buffer. In a preferred embodiment the polymerization agent is a thermostable DNA polymerase. Preferred DNA polymerases are Taq polymerase, Tth polymerase and Thermococcus litoralis polymerase. Taq polymerase is particularly preferred.

The antibody specific for the polymerization agent is used at a concentration effective to inhibit the polymerization agent at room temperature. The antibody may be monoclonal or polyclonal, or an antibody fragment. In a preferred embodiment, the antibody is monoclonal and is used at a molar ratio of from about 5 to about 500 over the polymerization agent. In a most preferred embodiment, the polymerization agent is Taq polymerase, the antibody is a monoclonal antibody specific for Taq polymerase, and the molar ratio of antibody to Taq polymerase is about 50:1. Exonuclease may be used at a concentration of from about 0.001 Units/$\mu$L to about 0.2 Units/$\mu$L. In a preferred embodiment, the exonuclease is Exo III and is used at a concentration of from about 0.0025 Units/$\mu$L to about 0.05 Units/$\mu$L. In another preferred embodiment the glycosylase is UNG. The skilled artisan can determine appropriate concentrations of antibody, exonuclease, and glycosylase, which may vary depending upon concentration of target and other experimental conditions. For example, various concentration ranges may be tested as taught in Examples VI and VII in order to determine the most effective concentrations.

In accordance with the present invention, it has been found that under certain PCR conditions, and in particular when oligonucleotide primers have overlapping regions capable of easily forming primer-dimers, amplification of target is so compromised that product may be undetectable. Agents alleged in the art to reduce zero cycle artifacts, such as anti-Taq antibody and Exo III, are individually incapable of relieving the artifacts to a degree that product becomes visually detectable. In the method of the present invention, the combination of an exonuclease and an antibody against the polymerization agent, or a glycosylase and the antibody, or the exonuclease, glycbsylase and antibody, detectably reduces primer-dimer formation and detectably increases efficiency of target amplification. In accordance with the present invention, a detectable increase or reduction is one which can be qualitatively visualized on an ethidium bromide stained gel by the ordinarily skilled artisan. Accordingly, the present invention provides a method of reducing formation of non-specific nucleic acids and increasing efficiency of amplification of a desired target in a PCR reaction. The present invention is particularly useful for PCR assays utilizing primers that readily form primer-dimers, and thus expands the choice of primers available for PCR.

Following contacting the sample with the reagents for PCR, the antibody, and at least one of the exonuclease and glycosylase, and prior to thermal cycling, the reaction mixture is heated to denature antibody, exonuclease and glycosylase and double-stranded DNA. In a preferred embodiment, the mixture is heated to about 85° C.–95° C. for about ten minutes. In methods utilizing glycosylase, and particularly UNG, a short incubation, for example, from two to five minutes, may be performed at about 50° C. to allow UNG to degrade primer-dimers. This incubation is performed prior to heat denaturation.

Following heat denaturation, standard PCR cycling of annealing, extending and denaturing is performed. Cycling parameters are known to the ordinarily skilled artisan, and can be easily adapted for particular conditions. The amplification method is preferably conducted in a continuous, automated manner. Appropriate instrumentation for automated PCR is well-known to the ordinarily skilled artisan and described, for example, in U.S. Pat. Nos. 4,965,188, 5,089,233 and 5,229,297. The skilled artisan can also easily detect amplified product, for example, by separating PCR products by agarose gel electrophoresis and visualizing by ethidium bromide staining, or detecting by hybridization with a labeled probe capable of hybridizing with the amplified nucleic acid or a variety of other detection methods well-known to one of ordinary skill in the art.

The present invention further provides a kit for PCR comprising a first container adapted to contain a polymerization agent, a second container adapted to contain an antibody specific to the polymerization agent, and a third container adapted to contain an exonuclease. In another embodiment, the kit further comprises a fourth container adapted to contain a glycosylase. The present invention also comprises a kit for PCR comprising a first container adapted to contain a polymerization agent, a second container adapted to contain an antibody specific for the polymerization agent, and a third container adapted to contain a glycosylase. Additional containers can also be provided for the inclusion of, for example, additional antibodies specific to the PCR polymerization agent. The kits of the present invention may also comprise reagents for PCR, including, for example, nucleoside triphosphates, primers and buffers.

In a preferred embodiment the polymerization agent is a DNA polymerase. In a more preferred embodiment the polymerase is Taq polymerase, Tth polymerase, or Thermococcus litoralis polymerase. Taq polymerase is particularly preferred. The preferred antibody is a monoclonal antibody specific for Taq polymerase. The glycosylase is preferably UNG. In another preferred embodiment, the exonuclease is Exo III, λ exonuclease or exonuclease I. Exo III is particularly preferred. The kits of the present invention are useful in increasing efficiency of amplification of target nucleic acids in PCR assays.

The following examples further illustrate the invention.

EXAXPLE I

Control of Primer-Dimer Formation with Exonuclease III and Tag-Antibody

This example utilizes a model system for primer-dimer formation in which primers were designed such that amplification of target cytomegalovirus DNA is of extremely low efficiency, and primer-dimer bands are prominent. While product bands cannot be visualized on ethidium bromide stained gels, more sensitive methods, such as hybridization capture followed by horseradish peroxidase-mediate oxidation of triarylimidazole leuco dye, indicate that a small amount of product is produced in the model system.

Oligonucleotide primers were prepared by solid phase phosphoramidite chemistry utilizing a Perkin-Elmer/Applied Biosystems Division Model 380B three column DNA synthesizer. Primers were biotinylated at the 5' end for non-radioactive detection. The primers employed were:
Primer JKCMV53: 5'-CATTCCCACT GACTTTCTGA CGCACGT-3' (SEQ ID NO:1)
Primer JKCMV55: 5'-TGAGGTCGTG GAACTTGATG GCGT-3' (SEQ ID NO:2)
The JKCMV primer set has a four nucleotide 3' overlapping region that forms primer-dimer complexes readily. The JKCMV primer concentration (0.8 μm) used was double the concentration typically used in PCR in order to further promote primer-dimer formation.

Exonuclease III (obtained from Promega) was tested alone at two different concentrations (2 and 6 Units per 100 μL PCR mix) and in combination with Taq antibody for ability to control primer-dimer formation. Taq antibody was used at a 50:1 molar ratio over Taq polymerase. Taq polymerase was prepared recombinantly as described in EP-A 0 482 714.

Monoclonal antibody (TP4-9.2) specific for Taq polymerase was prepared as described in U.S. Pat. No. 5,338,671 and was used in all examples unless otherwise indicated.

The PCR mix contained the following reagents:
10×PCR buffer (10 mM Tri·HCl, pH 8.0 with 50 mM KCl and 10 MM $MgCl_2$);
JKCMV 53/55 primers at 0.8 μM;
dNTPs (Sigma) at 1.5 mM each of DATP, dCTP, dGTP and dTTP;
Taq polymerase at 16 Units per 100 μL PCR mix; One unit is defined as the amount of enzyme activity required to incorporate 10 n moles of total nucleotides into an extending nucleic acid chain in 30 minutes at 74° C.;
Herring sperm DNA at 1 μg per 100 μL PCR mix; and
CMV cultured target at 100,000×final dilution (Control hCMV strain AD169 (ATCC VR538) was propagated in MRC-5 cells (ATCC CCL171) until characteristic cytopathic effect was evident in greater than 90% of the monolayer).

Following sample preparation, all samples were maintained at room temperature for two hours to allow primer-dimer formation. Samples in Group A underwent PCR immediately following the two hour incubation. Samples in Group B underwent an additional 20 minutes incubation at 40° C. before PCR. In Group C, Taq antibody and Exo III were added after the two hour room temperature incubation and before the 20 minute incubation at 40° C.

The following samples were tested in duplicate:
A. No additional inaubation after the 2 hours before PCR.
(1) No Taq antibody or Exo III (primer-dimer positive control);
(2) Taq antibody only (no Exo III);
(3) Exo III only [0.02 Units/μL or 2 Units/100 μL PCR mix];
(4) Exo III only [0.06 Units/μL or 6 Units/100 μL PCR mix];
(5) Taq antibody+Exo III [0.02 Units/μL or 2 Units/100 μL PCR mix];
(6) Taq antibody+Exo III [0.06 Units/μL or 6 Units/100 μL PCR mix].
B. Additional 40° C. 20 minute incubation before PCR for Exo III
(7) No Taq antibody or Exo III (primer-dimer positive control)
(8) Taq antibody only (no Exo III)
(9) Exo III only [0.02 Units/μL or 2 Units/100 μL PCR mix]
(10) Exo III only [0.06 Units/μL or 6 Units/100 μL PCR mix]
(11) Taq antibody+Exo III [0.02 Units/μL or 2 Units/100 μL PCR mix]
(12) Taq antibody+Exo III [0.06 Units/μL or 6 Units/100 μL PCR mix]
C. Taq antibody/Exo III added after the 2 hour RT incubation before 40° C. 20 minute additional incubation
(13) Taq antibody and Exo III (0.02 Units/μL or 2 Units/100 μL PCR mix)

(14) Taq antibody and Exo III (0.06 Units/μL or 6 Units/100 μL PCR mix)

PCR amplification was performed in the Clinical Diagnostics PCR Pouch described in U.S. Pat. No. 5,229,297 utilizing the Prototype Analyzer described in U.S. Pat. No. 5,089,233.

Standard PCR parameters were used following the 2 hour incubation or the 20 minute additional incubation. A preheat of the samples at 95° C. was used to heat denature the Taq antibody and Exonuclease III as well as to separate the double-stranded DNA in PCR mixture. 40 cycles of PCR then took place (95° C. for 15 seconds for melting and 68° C. for 35 seconds for annealing and extending). The PCR product was then collected from the PCR pouches and run on a 2.5% agarose gel stained with ethidium bromide. The gels were then photographed with a Polaroid camera.

PCR products and primer-dimer complexes were compared from sample to sample and the results were as follows:

| SAMPLE | Ab | Exo | PRODUCT BAND | PRIMER-DIMER BAND |
|---|---|---|---|---|
| A. No Additional Incubation | | | | |
| 1a | − | − | Negative | Strong Positive |
| 1b | − | − | Negative | Strong Positive |
| 2a | + | − | Negative | Positive |
| 2b | + | − | Negative | Positive |
| 3a | − | 2U | Negative | Strong Positive |
| 3b | − | 2U | Negative | Strong Positive |
| 4a | − | 6U | Negative | Strong Positive |
| 4b | − | 6U | Negative | Strong Positive |
| 5a | + | 2U | Strong Positive | Negative |
| 5b | + | 2U | Strong Positive | Very Weak Negative |
| 6a | + | 6U | Positive | Very Weak Negative |
| 6b | + | 6U | Positive | Very Weak Negative |
| B. Additional 40° C. 20 Minute Incubation | | | | |
| 7a | − | − | Negative | Strong Positive |
| 7b | − | − | Negative | Strong Positive |
| 8a | + | − | Negative | Strong Positive |
| 8b | + | − | Negative | Strong Positive |
| 9a | − | 2U | Negative | Strong Positive |
| 9b | − | 2U | Negative | Strong Positive |
| 10a | − | 6U | Negative | Weak Positive |
| 10b | − | 6U | Negative | Weak Positive |
| 11a | + | 2U | Negative | Positive |
| 11b | + | 2U | Weak Positive | Positive |
| 12a | + | 6U | Positive | Very Weak Positive |
| 12b | + | 6U | Negative | Very Weak Positive |
| C. Taq Ab and Exo III added after 2 hour incubation, Prior 40° C. 20 minute incubation | | | | |
| 13a | + | 2 | Negative | Positive |
| 13b | + | 2 | Weak Positive | Positive |
| 14a | + | 6 | Weak Positive | Weak Positive |
| 14b | + | 6 | Weak Positive | Weak Positive |

From the gel results, it can be seen that Sample #5, which was the combination of Taq antibody and Exo III at 0.02 Units per μL or 2 Units per 100 μL PCR mix with no additional incubation, had the most efficient PCR amplification efficiency and primer-dimer control. Slightly lower signal PCR product bands and equivalent primer-dimer control were produced by Sample #6, which was the combination of Taq antibody and Exo III at 0.06 Units per μL or 6 Units per 100 μL PCR mix with no additional incubation. Weak PCR product bands were achieved with Samples #11 and #12, which were the combination of Taq antibody and Exo III at both concentrations with the additional incubation. Samples #13 and #14 were the most stringent test of Exonuclease III's ability to suppress primer-dimer formation as the samples were left out for 2 hours at room temperature without Taq antibody and Exo III in the PCR mix. Then after the 2 hours, both Taq antibody and Exo III were added, and the samples were held at 40° C. for 20 minutes to allow Exo III to degrade the preformed primer-dimer. Slight PCR bands were produced with weaker primer-dimer bands compared to other samples, showing the positive effect Exo III has on PCR amplification efficiency by controlling primer-dimer formation.

This example demonstrates that the use of Exo III alone or Taq antibody alone fails to suppress primer-dimer formation or increase efficiency, whereas a combination of Exo III and Taq antibody increased PCR amplification efficiency and controlled primer-dimers, even under the most challenging (Group C) conditions.

EXAMPLE II

This example compares the ability of Exo III and Taq antibody relative to either agent alone to control primer-dimer formation during three and four hour incubations. Further, since clinical samples vary in the level of background DNA, the effect of background DNA on the ability of Exo III and Taq antibody to control primer-dimer formation was also assessed.

The PCR sample mix contained the following reagents:

10×PCR buffer with 10 mM magnesium;

JKCMV 53/55 primers at 0.8 μM;

Sigma dNTPs at 1.5 mM each;

Taq polymerase at 16 Units per 100 μL PCR mix;

CMV cultured target at 100,000×final dilution. Samples in Group B (Samples 7–12) further contained herring sperm DNA at 1 μg per 100 μL PCR mix. Taq antibody (at a 50:1 molar ratio over Taq polymerase) and Exo III (2 or 6 Units per 100 μL PCR mix) were tested alone and in combination for both Group A and Group B samples.

The following samples were prepared:

A. No Background DNA (1) No Taq antibody or Exo III (primer-dimer positive control);

(2) Taq antibody only (no Exo III);

(3) Exo III only [0.02 Units/μL or 2 Units 100 μL PCT mix];

(4) Exo III only [0.06 Units/μL or 6 Units/100 μL PCR mix];

(5) Taq antibody+Exo III [0.02 Units/μL or 2 Units/100 μL PCR mix]; and (6) Taq antibody+Exo III [0.06 Units/μL or 6 Units/100 μL PCR mix];

B. Background DNA Included (7) No Tag antibody or Exo III (primer-dimer positive control);

(8) Tag antibody only (no Exo III);

(9) Exo III only [0.02 Units/μL or 2 Units/100 μL PCR mix];

(10) Exo III only [0.06 Units/μL or 6 Units/100 μL PCR mix];

(11) Tag antibody+Exo III [0.02 Units/μL or 2 Units/100 μL PCR mix];

(12) Tag antibody+Exo III [0.06 Units/μL or 6 Units/100 μL PCR mix].

Samples were left out at room temperature for either three or four hours to allow primer-dimer formation to occur prior to PCR amplification. PCR amplification was performed in the Clinical Diagnostics Pouch utilizing the Prototype Analyzer. A preheat of the samples at 95° C. was used to heat denature the Tag antibody and Exonuclease III as well as to separate the double-stranded DNA in the PCR mixture. 40 cycles of PCR then took place (95° C. for 15 second for melting and 68° C. for 35 seconds for annealing and extending). The PCR product was then collected from the PCR pouches and run on a 2.5% agarose gel stained with ethidium bromide. The gels were then photographed with a Polaroid camera.

PCR products and primer-dimer complexes were compared from sample to sample and the results were as follows:

| SAMPLE | Ab | Exo | PRODUCT BAND | PRIMER-DIMER BAND |
|---|---|---|---|---|
| (1) 3 Hour Room Temperature Incubation ||||| 
| A. No Background DNA ||||| 
| 1 | − | − | Negative | Strong Positive |
| 2 | + | − | Weak Positive | Positive |
| 3 | − | 2U | Very Weak Positive | Strong Positive |
| 4 | − | 6U | Negative | Positive |
| 5 | + | 2U | Strong Positive | Very Weak Positive |
| 6 | + | 6U | Negative | Negative |
| B. Background DNA ||||| 
| 7 | − | − | Negative | Strong Positive |
| 8 | + | − | Positive | Positive |
| 9 | − | 2U | Negative | Positive |
| 10 | − | 6U | Negative | Weak Positive |
| 11 | + | 2U | Strong Positive | Negative |
| 12 | + | 6U | Negative | Negative |
| (2) 4 Hour Room Temperature Incubation ||||| 
| A. No Background DNA ||||| 
| 1 | − | − | Negative | Strong Positive |
| 2 | + | − | Strong Positive | Positive |
| 3 | − | 2U | Weak Positive | Strong Positive |
| 4 | − | 6U | Very Weak Positive | Positive |
| 5 | + | 2U | Strong Positive | Very Weak Negative |
| 6 | + | 6U | Strong Positive | Negative |
| B. Background DNA ||||| 
| 7 | − | − | Negative | Strong Positive |
| 8 | + | − | Positive | Positive |
| 9 | − | 2U | Very Weak Positive | Positive |
| 10 | − | 6U | Negative | Positive |
| 11 | + | 2U | Very Strong Positive | Negative |
| 12 | + | 6U | Strong Positive | Negative |

The gel results showed that for samples incubated for three hours at room temperature prior to PCR, amplification efficiency was increased and primer-dimer formation reduced for samples #5 and #11, which contained the combination of Taq antibody and Exo III (0.02 Units per $\mu$L) in the absence and presence of background DNA, respectively. For the four hour incubation, samples #5 (Taq Ab, 0.02 Units Exo III per $\mu$L, no background DNA), #6 (Taq Ab, 0.06 Units Exo III per $\mu$L, no background DNA), #11 (Taq Ab, 0.02 Units Exo III per $\mu$L, background DNA), and #12 (Taq Ab, 0.06 Units Exo III per $\mu$L, background DNA) exhibited increased amplification efficiency and reduced primer-dimer formation. These results confirm Example I results that the combination of Taq antibody and Exonuclease III increases PCR amplification efficiency and primer-dimer control, and demonstrate that the combination of Taq antibody and Exonuclease III is effective in the presence or absence of background DNA and long room temperature incubations prior to PCR. Such robustness is critical to practical systems for clinical use and is achieved only through the use of a combination of elements as described above.

EXAMPLE III

Uracil N-glycosylase (UNG) and Taq antibody were tested alone and in combination with Exo III for control of primer-dimer formation and effect on amplification efficiency in PCR. The Clinical Diagnostic's PCR pouch and prototype analyzer were used for this experiment. The PCR mix had dUTP substituted for dTTP and lower magnesium levels for UNG usage and was as follows:

10×PCR buffer with 5 mM magnesium;

JKCMV 53/55 primers at 0.8 $\mu$M each;

DATP, dCTP and dGTP at 0.2 mM each;

dUTP at 0.4 mM;

Taq polymerase at 8 Units per 100 $\mu$L PCR mix;

Herring sperm DNA at 1 $\mu$g per 100 $\mu$L PCR mix;

CMV cultured target at 100,000×final dilution.

Samples were prepared containing UNG and Taq antibody alone or in combinations with Exo III at the concentrations described below. Antibody was used at 50:1 molar ratio over Tag polymerase. UNG was obtained from Perkin-Elmer. The following samples were prepared.

(1) No antibody, UNG, or Exo III (primer-dimer positive control);

(2) Antibody only;

(3) UNG only [1 Unit/100 $\mu$L PCR mix];

(4) Antibody and UNG [1 Unit/100 $\mu$L PCR mix];

(5) Antibody and UNG [2 Units/100 $\mu$L PCR mix];

(6) Antibody and Exo III [2 Units/100 $\mu$L PCR mix];

(7) Antibody, UNG, and Exo III [1 Unit and 2 Units/100 $\mu$L PCR mix respectively];

(8) Antibody, UNG, and Exo III [2 Units/100 $\mu$L PCR mix each].

All samples were left out at room temperature for 2–3 hours prior to PCR to allow primer-dimer formation to occur. Single samples were tested at the end of 2 hours and duplicate samples were tested at the end of 3 hours. Additional preamplification conditions were needed after the 2 or 3 hour room temperature incubation for UNG usage and were as follows: (1) 2 minute 50° C. incubation for UNG primer-dimer degradation, and (2) 10 minute 95° C. incubation for UNG denaturation. Standard PCR cycling parameters were used immediately following these additional incubations (95° C. for 15 seconds for melting and 68° C. for 35 seconds for annealing and extending). The PCR products were collected from the pouches immediately following PCR and were run on a 2.5% agarose gel stained with ethidium bromide. The gels were photographed with a Polaroid camera.

PCR products and primer-dimer complexes were compared from sample to sample and the results were as follows:

| SAMPLE | Ab | Exo III | UNG | PRODUCT BAND | PRIMER-DIMER BAND |
|---|---|---|---|---|---|
| A. 2 Hour Room Temperature Incubation | | | | | |
| 1 | − | − | − | Negative | Strong Positive |
| 2 | + | − | − | Very Weak Positive | Positive |
| 3 | − | 1U | − | Negative | Strong Positive |
| 4 | + | 1U | − | Very Weak Positive | Positive |
| 5 | + | 2U | − | Very Weak Positive | Positive |
| 6 | + | − | 2U | Strong Positive | Weak Positive |
| 7 | + | 1U | 2U | Strong Positive | Very Weak Positive |
| 8 | + | 2U | 2U | Strong Positive | Very Weak Positive |
| B. 3 Hour Room Temperature Incubation | | | | | |
| 1a | − | − | − | Negative | Strong Positive |
| 1b | − | − | − | Negative | Strong Positive |
| 2a | + | − | − | Very Weak Positive | Positive |
| 2b | + | − | − | Very Weak Positive | Positive |
| 3a | − | 1U | − | Negative | Strong Positive |
| 3b | − | 1U | − | Negative | Strong Positive |
| 4a | + | 1U | − | Very Weak Positive | Positive |
| 4b | + | 1U | − | Very Weak Positive | Positive |
| 5a | + | 2U | − | Negative | Strong Positive |
| 5b | + | 2U | − | Very Weak Positive | Positive |
| 6a | + | − | 2U | Positive | Weak Positive |
| 6b | + | − | 2U | Strong Positive | Very Weak Positive |
| 7a | + | 1U | 2U | Strong Positive | Weak Positive |
| 7b | + | 1U | 2U | Strong Positive | Very Weak Positive |
| 8a | + | 2U | 2U | Strong Positive | Weak Positive |
| 8b | + | 2U | 2U | Strong Positive | Very Weak Positive |

From the gel results, it can be seen that Samples #6, #7 and #8 gave the best results for both the 2 and 3 hour room temperature incubations. Samples #6 (antibody and Exo III at 0.2 Units per 100 μL PCR mix) confirms earlier results obtained in Examples I and II. Samples #7 and #8 (antibody, UNG at 1 and 2 Units per 100 μL PCR mix respectively, and Exo III at 2 Units per 100 μL PCR mix in both samples) show that the combination of antibody, UNG, and Exo III improves PCR amplification efficiency by further reducing primer-dimer formation when compared to any of the agents alone or with just two of the three agents combined. Antibody or UNG alone gave very weak if any product bands and very strong primer-dimer bands. Antibody and Exo III gave good results with strong product bands, but the combination of all three methods gave even weaker primer-dimer bands and strong product bands.

EXAMPLE IV

Uracil-N-glycosylase, Exo III and a combination of two Taq antibodies were tested alone and in combination for control of primer-dimer formation and their effect on the amplification efficiency in PCR. The Clinical Diagnostic's PCR pouch and prototype analyzer were used in this experiment. The PCR mix had dUTP substituted for dTTP and lower magnesium levels for UNG usage and was as follows:

10×PCR buffer with 5im magnesium;

JKCMV 53/55 primers at 0.8 Am each;

DATP, dCTP and dGTP at 0.2 mM each;

dUTP at 0.4 mM;

Taq polymerase at 8 units per 100 μL PCR mix;

Herring sperm DNA at 1 μg per 100 μL PCR mix;

CMV cultured target at 100,000×final dilution.

Samples were prepared containing UNG and Taq antibodies alone or in combination with Exo III at the combinations described below. The Taq antibody combination used consisted of TP4-9.2 at a 5:1 molar ratio over Taq polymerase, and Taq antibody TP1-12.2 at a 50:1 molar ratio over Taq polymerase. UNG was obtained from Perkin-Elmer. The following samples were prepared.

(1) No antibody, UNG or Exo III (primer-dimer positive control);

(2a,b) UNG only [1 Unit/100 μL PCR mix];

(3a,b) UNG only [2 Units/100 μL PCR mix];

(4) Antibodies only;

(5) Exo III only [2 Units/100 μL PCR mix];

(6a,b) Antibodies and UNG [1 Unit/100 μL PCR mix];

(7a,b) Antibodies and UNG [2 Units/100 μL PCR mix];

(8) Antibodies and Exo III [2 Units/100 μL PCR mix];

(9a,b) Antibodies, UNG and Exo III [1 Unit and 2 Units/100 μL PCR mix, respectively];

(10a,b) Antibodies, UNG and Exo III [2 Units/100 μL PCR mix each].

All samples were left at room temperature for 2 hours prior to PCR to allow primer-dimer formation to occur. Additional preamplification conditions were needed after the 2 hour incubation for UNG usage and were as follows: (1) 2 minute 50° C. incubation for UNG primer-dimer degradation, and (2) 10 minute 95° C. incubation for UNG denaturation. Standard PCR cycling parameters were used immediately following these additional incubations (95° C. for 15 seconds for melting and 68° C. for 35 seconds for annealing and extending). The PCR products were collected immediately following PCR and were run on a 2.5% agarose gel stained with ethidium bromide. The gels were photographed with a Polaroid camera.

PCR products and primer-dimer complexes were compared from sample to sample and the results were as follows:

| SAMPLE | Abs | Exo UNG | III | PRODUCT BAND | PRIMER-DIMER BAND |
|---|---|---|---|---|---|
| 1 | − | − | − | Negative | Strong Positive |
| 2a | − | 1U | − | Negative | Strong Positive |
| 2b | − | 1U | − | Negative | Strong Positive |
| 3a | − | 2U | − | Negative | Strong Positive |
| 3b | − | 2U | − | Negative | Strong Positive |
| 4 | + | − | − | Very Weak Positive | Positive |
| 5 | − | − | 2U | Negative | Strong Positive |
| 6a | + | 1U | − | Positive | Weak Positive |
| 6b | + | 1U | − | Positive | Weak Positive |
| 7a | + | 2U | − | Positive | Weak Positive |
| 7b | + | 2U | − | Positive | Weak Positive |
| 8 | + | − | 2U | Strong Positive | Negative |
| 9a | + | 1U | 2U | Strong Positive | Negative |
| 9b | + | 1U | 2U | Strong Positive | Negative |

-continued

| SAMPLE | Abs | Exo UNG | III | PRODUCT BAND | PRIMER-DIMER BAND |
|---|---|---|---|---|---|
| 10a | + | 2U | 2U | Strong Positive | Weak Positive |
| 10b | + | 2U | 2U | Strong Positive | Very Weak Positive |

From the gel results it can be seen that Samples #8, #9(a,b) and #10(a,b) gave the best results for this experiment. UNG only and Exo III only samples (#2, #3 and #5) gave no detectable product bands and very strong primer-dimer bands equivalent to the primer-dimer positive control sample (#1) while Taq antibody alone (#4) gave a very weak product band and a positive primer-dimer band. These results show the ineffectiveness of each of these three methods at preventing primer-dimer formation thus decreasing the amplification efficiency of the target sequence. The combinations of UNG and antibodies (Samples #6 and #7), antibodies and Exo III (Sample #8), and all three together (Samples #9 and 10) gave very strong product bands when compared to any of the methods alone, and these same combinations reduced the amount of primer-dimer formed drastically to where it was not detectable in some samples. The combination of UNG or Exo III with Taq antibodies or a combination of all three together increase the amplification efficiency of the PCR reaction as well as decrease the amount of primer-dimer and other side products formed in PCR, resulting in an increase in both the sensitivity and specificity of this powerful diagnostic device.

EXAMPLE V

In this experiment various combinations of UNG, Exo III and Taq antibody were tested for control of primer-dimer formation prior to PCR amplification. Two PCR model systems having different characteristics than the JKCMV 53/55 PCR model system were used. The two PCR model systems used were as follows: (1) SMA 7/SMA 20 HIV GAG PCR system; and (2) SK38/BW17 HIV PCR system. The SMA 7/20 PCR system has a 4 nucleotide base pair overlap one base pair inside the 3' end of the primers. The SK38/BW17 primer system has a 3' 2 nucleotide base pair overlap, compared to the 3' 4 nucleotide base pair overlap of the JKCMV 53/55 primer system. The primers have the following sequences:

Primer SMA7: 5'-AGTGGGGGGA CATCAAGCAG CCATGCAA-3' (SEQ ID NO:3)
Primer SMA20: 5'-CCTGCTATGT CACTTCCCCT TGGTTCTCTC-3' (SEQ ID NO:4)
Primer SK38: 5'-ATAATCCACC TATCCCAGTA GGAGAAAT-3' (SEQ ID NO:5)
Primer BW17: 5'-TTTGGTCCTT GTCTTATGTC CAGAATGC-3' (SEQ ID NO:6).

The PCR mix had dUTP substituted for dTTP and lower magnesium levels for UNG usage and was as follows:
10×PCR buffer with 5 mM magnesium;
SMA 7/20 and SK38/BW17 primers at 0.8 μM each;
dATP, dCTP and dGTP at 0.2 mM each;
dUTP at 0.4 mM;
Taq polymerase at 8 Units per 100 μL PCR mix;
Herring sperm DNA at 1 μG per 100 μL PCR mix;
HIV target at 100 copies/100 μL (obtained from 8E5/LAV cell line containing a single integrated copy of the HIV-1 genome).

Samples were prepared with Taq antibody (at 50:1 molar ratio over Taq polymerase) and UNG alone and in various combinations with Exo III as follows:

(1) No antibody, UNG, Exo III (primer-dimer positive control);
(2) Antibody only;
(3) UNG only [1 Unit/100 μL PCR mix];
(4) Antibody and UNG [1 Unit/100 μL PCR mix];
(5) Antibody and UNG [2 Units/100 μL PCR mix];
(6) Antibody and Exo III [2 Units/100 μL PCR mix];
(7) Antibody, UNG and Exo III [1 Unit and 2 Units/100 μL PCR mix, respectively];
(8) Antibody, UNG and Exo III [2 Units/100 μL PCR mix each].

The Clinical Diagnostic's PCR Pouch and Prototype Analyzer were used for this experiment. All samples were left out at room temperature for 4 hours prior to PCR to allow primer-dimer formation to occur. Additional preamplification conditions were needed after the 4 hour room temperature incubation for UNG usage and were as follows: (1) 2 minute 50° C. incubation for UNG primer-dimer degradation, and (2) 10 minute 95° C. incubation for UNG denaturation. Standard PCR cycling parameters for these two model systems were used immediately following these additional incubations (95° C. for 15 seconds for melting and 64° C. for 35 seconds for annealing and extending). The PCR product was collected from the pouches immediately following PCR and were run on a 2.5% agarose gel stained with ethidium bromide. The gels were then photographed with a Polaroid camera.

PCR products and primer-dimer complexes were compared from sample to sample and the results were as follows:

| SAMPLE | Ab | UNG | Exo III | PRODUCT BAND | PRIMER-DIMER BAND |
|---|---|---|---|---|---|
| A. SMA 7/20 PCR Model System | | | | | |
| 1 | − | − | − | Negative | Strong Positive |
| 2 | + | − | − | Weak Positive | Positive |
| 3 | − | 1U | − | Negative | Strong Positive |
| 4 | + | 1U | − | Weak Positive | Strong Positive |
| 5 | + | 2U | − | Weak Positive | Strong Positive |
| 6 | + | − | 2U | Positive | Positive |
| 7 | + | 1U | 2U | Strong Positive | Positive |
| 8 | + | 2U | 2U | Strong Positive | Positive |
| B. SK38/BW17 PCR Model System | | | | | |
| 1 | − | − | − | Negative | Strong Positive |
| 2 | + | − | − | Positive | Positive |
| 3 | − | 1U | − | Positive | Positive |
| 4 | + | 1U | − | Strong Positive | Weak Positive |
| 5 | + | 2U | − | Strong Positive | Weak Positive |
| 6 | + | − | 2U | Strong Positive | Very Weak Positive |
| 7 | + | 1U | 2U | Strong Positive | Very Weak Positive |
| 8 | + | 2U | 2U | Weak Positive | Very Weak Positive |

From the gel results, it can be seen that for both primer systems there are no detectable PCR product bands and strong primer-dimer bands in the absence of antibody, Exo III or UNG (Sample #1). The SMA 7/20 PCR primer system results show weak PCR product bands with Taq antibody alone and with UNG (Samples #2, #4 and #5), while strong PCR product bands are observed for the combination of Taq antibody, UNG and Exo III (Samples #7 and #8). Primer-dimer bands are reduced compared to Samples #1, #3, #4 and #5 as well. These results agree with the results obtained in Examples III and IV with the JKCMV 53/55 PCR system that the combination of all three triggering methods significantly enhances primer-diner control and increases PCR amplification efficiency.

The SK38/BW17 PCR primer system results are slightly varied from the previous results due to less severe primer-dimer formation with this system owing to less extensive 3' homology. Good results are obtained for Taq antibody alone (Sample #2) and UNG alone (Sample #3) when compared to Sample #1. However, an immediate enhancement in triggering is seen with Tag antibody+UNG (Samples #4 and #5), Taq antibody+Exo III (Samples #6) and the combination of all 3 triggering methods (Sample #7). From this experiment, it can be concluded that combining Taq antibody with Exonuclease III or Uracil n-glycosylase or both enhances PCR triggering and thus increases PCR amplification efficiencies.

EXAMPLE VI

The concentrations range of Exonuclease III that enhances Taq antibody triggering of PCR product amplification was determined in this experiment. The JKCMV 53/55 primer set was used, which has a four nucleotide 3' overlapping region that forms primer-dimer complexes readily. The Clinical Diagnostic's PCR pouch and prototype analyzer were used for this experiment. The PCR mix contained the following reagents:

10×PCR buffer with 5 mM magnesium;
JKCMV 53/55 primers at 0.8 $\mu$M;
dATP, dCTP, dGTP at 0.2 mM each;
dUTP at 0.4 mM;
Taq polymerase at 8 Units per 100 $\mu$L PCR mix;
Herring sperm DNA at 1 $\mu$g per 100 $\mu$L PCR mix;
CMV cultured target at 100,000×final dilution.

Taq antibody (50:1 molar ratio over Taq polymerase) was added to all samples except the control (Sample 1).

Exonuclease III was added to samples as indicated from a concentration of 0.001 Units/$\mu$L (or 0.1 Units per 100 $\mu$L PCR mix) to 0.2 Units/$\mu$L (or 20 Units per 100 $\mu$L PCR mix). The following samples were tested:

(1) No Taq antibody or Exo III (primer-dimer positive control);
(2) Taq antibody only;
(3) Taq Ab+Exo III (0.001 U/$\mu$L or 0.1 U/100 $\mu$L PCR mix);
(4) Taq Ab+Exo III (0.0025 U/$\mu$L or 0.25 U/100 $\mu$L PCR mix);
(5) Taq Ab+Exo III (0.005 U/$\mu$L or 0.5 U/100 $\mu$L PCR mix);
(6) Taq Ab+Exo III (0.0075 U/$\mu$L or 0.75 U/100 $\mu$L PCR mix);
(7) Taq Ab+Exo III (0.01 U/$\mu$L or 1 U/100 $\mu$L PCR mix);
(8) Taq Ab+Exo III (0.0025 U/$\mu$L or 2.5 U/100 $\mu$L PCR mix);
(9) Taq Ab+Exo III (0.05 U/$\mu$L or 5 U/100 $\mu$L PCR mix);
(10) Tag Ab+Exo III (0.1 U/$\mu$L or 10 U/100 $\mu$L PCR mix);
(11) Tag Ab+Exo III (0.15 U/$\mu$L or 15 U/100 $\mu$L PCR mix);
(12) Taq Ab+Exo III (0.2 U/$\mu$L or 20 U/100 $\mu$L PCR mix).

All samples were incubated at room temperature for 2 hours before PCR. No additional incubations were used before standard PCR parameters were used. A preheat of the samples at 95° C. for 180 seconds was used to heat denature both the Taq antibody and Exonuclease III as well as to separate the double-stranded DNA in the PCR mixture. Forty cycles of PCR were performed (95° C. for 15 seconds for melting and 68° C. for 35 seconds for annealing and extending). The PCR product was then collected form the PCR pouches and run on a 2.5% agarose gel stained with ethidium bromide. The gels were then photographed with a Polaroid camera.

PCR products and primer-dimer complexes were compared from sample to sample and the results were as follows:

| SAMPLE | PRODUCT BAND | PRIMER-DIMER BAND |
|--------|--------------|-------------------|
| 1 | Negative | Strong Positive |
| 2 | Positive | Positive |
| 3 | Weak Positive | Positive |
| 4 | Positive | Positive |
| 5 | Positive | Positive |
| 6 | Strong Positive | Weak Positive |
| 7 | Strong Positive | Very Weak Positive |
| 8 | Strong Positive | Negative |
| 9 | Positive | Negative |
| 10 | Negative | Negative |
| 11 | Negative | Negative |
| 12 | Negative | Negative |

From these data, it was determined that a range of 0.0025 Units per $\mu$L to 0.05 Units per $\mu$L (0.25 Units to 5 Units per 100 $\mu$L PCR mix) of Exonuclease III was effective for enhancing Taq antibody triggering with optimal results obtained at concentrations of 0.0075 Units to 0.025 Units per $\mu$L (0.75 Units to 2.5 Units per 100 $\mu$L PCR mix) of Exonuclease III.

EXAMPLE VII

The concentration range of UNG that enhances Tag antibody triggering in the presence or absence of Exo III was determined in this experiment. The JKCMV 53/55 primer set was used, which has a 4 nucleotide 3' overlapping region that forms primer-dimer complexes readily. The Clinical Diagnostic's PCR pouch and prototype analyzer were used for this experiment. The PCR mix contained the following reagents:

10×PCR buffer with 5 mM magnesium;
JKCMV 53/55 primers at 0.8 $\mu$M;
DATP, cDTP, dGTP at 0.2 mM each;
dUTP at 0.4 mM;
Tag polymerase at 8 Units per 100 $\mu$L PCR mix;
Herring sperm DNA at 1 $\mu$g per 100 $\mu$L PCR mix;
CMV cultured target at 100,000×final dilution;
Tag antibody (50:1 molar ratio over Tag Polymerase) was added to all samples except the control (Sample 1).

UNG was added to samples from a concentration of 0.0001 Units/$\mu$L (or 0.01 Units per 100 $\mu$L PCR mix). The following samples were tested both in the presence (+) and absence (−) of Exo III at 0.02 Units/$\mu$L or 2 Units per 100 $\mu$L PCR mix.

(1) No Tag antibody or UNG (primer-dimer positive control);
(2) Tag antibody only;
(3) Tag Ab+UNG (0.0001 U/$\mu$L or 0.01 U/100 $\mu$L PCR mix);
(4) Tag Ab+UNG (0.0005 U/$\mu$L or 0.05 (U/100 $\mu$L PCR mix);

(5) Taq Ab+UNG (0.001 U/µL or 0.1 U/100 µL PCR mix);
(6) Taq Ab+UNG (0.005 U/µL or 0.5 U/100 µL PCR mix);
(7) Taq Ab+UNG (0.01 U/µL or 1 U/100 µL PCR mix);
(8) Taq AB+UNG (0.02 U/µL or 2 U/100 µL PCR mix).

All samples were incubated at room temperature for 2 hours before PCR. A preheat of the samples at 95° C. for 10 minutes was used to heat denature the UNG (as required), Taq antibody and Exonuclease III as well as to separate the double-stranded DNA in the PCR mixture. 40 cycles of PCR then took place (95° C. for 15 seconds for melting and 68° C. for 35 seconds for annealing and extending). The PCR product was then collected immediately from the PCR pouches and run on a 2.5% agarose gel stained with ethidium bromide as to not allow UNG renaturation. The gels were then photographed with a Polaroid camera.

PCR products and primer-dimer complexes were compared from sample to sample and the results were as follows:

| SAMPLE | PRODUCT BAND | PRIMER-DIMER BAND |
| --- | --- | --- |
| 1 (−Exo III) | Negative | Strong Positive |
| 2 (−Exo III) | Negative | Positive |
| 3 (−Exo III) | Negative | Positive |
| 4 (−Exo III) | Negative | Positive |
| 5 (−Exo III) | Negative | Positive |
| 6 (−Exo III) | Very Weak Positive | Weak Positive |
| 7 (−Exo III) | Weak Positive | Very Weak Positive |
| 8 (−Exo III) | Weak Positive | Very Weak Positive |
| 1 (+Exo III) | Negative | Strong Positive |
| 2 (+Exo III) | Positive | Negative |
| 3 (+Exo III) | Strong Positive | Negative |
| 4 (+Exo III) | Strong Positive | Negative |
| 5 (+Exo III) | Strong Positive | Very Weak Positive |
| 6 (+Exo III) | Strong Positive | Negative |
| 7 (+Exo III) | Strong Positive | Negative |
| 8 (+Exo III) | Strong Positive | Negative |

From these data, it can be seen that the range of UNG that is effective on controlling primer-dimer formation with Taq antibody is dependent on whether Exonuclease III is included in the sample or not. For samples without Exo III, UNG showed enhanced triggering at concentrations between 0.005–0.02 Units per µL (0.5–2 Units per 100 µL PCR mix). For samples with Exo III, an immediate positive effect was seen with the first concentration of UNG tested (0.0001 Units per µL or 0.01 Units per µL). This positive effect was demonstrated for all concentrations of UNG added up through 0.02 Units per µL or 2 Units per 100 µL PCR mix. No higher concentrations of UNG were tested due to the relatively low concentration of the stock sample (1 Unit per µL) and its high cost. This does not mean, however, that a higher concentration of UNG would not work.

What is claimed is:

1. A method for the amplification of a target nucleic acid comprising:
   (a) contacting a sample suspected of containing said target nucleic acid with (i) a thermostable nucleic acid polymerization agent, (ii) two oligonucleotide primers that are substantially complementary to regions of said target nucleic acid to hybridize thereto wherein said oligonucleotide primers comprise homologous base pairs at the 3' termini and are capable of extension by the nucleic acid polymerization agent to form primer-dimer, (iii) four different nucleoside triphosphates, and (iv) an antibody specific to said polymerization agent that is capable of inhibiting said polymerization agent and that is inactivated at elevated temperatures and an exonuclease that attacks double-stranded DNA, or said antibody specific to said polymerization agent and said exonuclease and a glycosylase to form a reaction admixture wherein the amount of said exonuclease is less than or equal to about 6 Units per 100 microliters of said reaction admixture;
   (b) heating said reaction admixture to denature said antibody, said exonuclease and said glycosylase;
   (c) forming primer extension products; and
   (d) thereby amplifying the target nucleic acid and reducing primer-dimer formation.

2. The method of claim 1 wherein said target nucleic acid is DNA or RNA.

3. The method of claim 1 wherein said nucleoside triphosphates are deoxyribonucleoside triphosphates.

4. The method of claim 3 wherein said deoxyribonucleoside triphosphates are dATP, dGTP, dCTP and dTTP.

5. The method of claim 3 wherein said deoxyribonucleoside triphosphates are dATP, dGTP, dCTP and dUTP.

6. The method of claim 1 wherein said polymerization agent is a DNA polymerase.

7. The method of claim 6 wherein said DNA polymerase is selected from the group consisting of thermus aquaticus (Taq) polymerase, thermus thermophilus polymerase and Thermococcus litoralis polymerase.

8. The method of claim 1 wherein said antibody is a monoclonal antibody or a polyclonal antibody.

9. The method of claim 1 wherein said exonuclease is selected from the group consisting of exonuclease I, exonuclease III, λ exonuclease, T7 exonuclease, ribonuclease II, polynucleotide phosphorylase and BAL31 nuclease.

10. The method of claim 1 wherein said exonuclease is exonuclease III.

11. The method of claim 1 wherein said glycosylase is uracil-N-glycosylase.

12. The method of claim 1 wherein said heating is from about 85° C. to about 95° C.

13. The method of claim 1 wherein said thermostable polymerization agent is Taq polymerase, said antibody is a monoclonal antibody against Taq polymerase, said exonuclease is exonuclease III, and said glycosylase is uracil-N-glycosylase.

14. The method of claim 8 wherein said monoclonal antibody is selected from the group consisting of TP4-9.2 produced by hybridoma ATCC No. HB11807, TP1-12.2 produced by hybridoma ATCC No. HB11127, and both TP4-9.2 and TP1-12.2.

15. The method of claim 1 which further comprises detecting primer extension products.

16. The method of claim 15 wherein said detection is accomplished by measuring fluorescence changes induced by binding of a fluorescent compound to double-stranded DNA.

17. An admixture for use in PCR comprising a polymerization agent, two oligonucleotide primers comprising homologous base pairs at the 3' termini that are capable of extension by said polymerization agent to form primer-dimer, and an antibody specific to said polymerization agent that is capable of inhibiting said polymerization agent and an exonuclease that attacks double stranded DNA, or said antibody specific to said polymerization agent and said exonuclease and a glycosylase, wherein the amount of said exonuclease during amplification is less than or equal to about 6 Units per 100 microliters.

18. The admixture of claim 17 further comprising four different nucleoside triphosphates.

19. The admixture of claim 17 further comprising said polymerization agent which is thermostable.

20. The admixture of claim 19 wherein said polymerization agent is a DNA polymerase.

21. The admixture of claim 20 wherein said DNA polymerase is selected from the group of thermus aquaticus (Taq) polymerase, thermus thermophilus polymerase and Thermococcus litoralis polymerase.

22. The admixture of claim 17 wherein said antibody is a monoclonal antibody or a polyclonal antibody.

23. The admixture of claim 17 wherein said exonuclease is selected from the group of exonuclease I, exonuclease III and λ exonuclease.

24. The admixture of claim 23 wherein said exonuclease is exonuclease III.

25. The admixture of claim 17 wherein said glycosylase is uracil-N-glycosylase.

26. The admixture of claim 22 wherein said monoclonal antibody is selected from the group consisting of TP4-9.2 produced by hybridoma ATCC No. HB11807, TP1-12.2 produced by hybridoma ATCC No. HB11127, and both TP4-9.2 and TP1-12.2.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
(A) LENGTH: 27 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:1:

CATTCCCACT GACTTTCTGA CGCACGT                27

(2) INFORMATION FOR SEQ ID NO:2:

(i) SEQUENCE CHARACTERISTICS:
(A) LENGTH: 24 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:2:

TGAGGTCGTG GAACTTGATG GCGT                   24

(2) INFORMATION FOR SEQ ID NO:3:

(i) SEQUENCE CHARACTERISTICS:
(A) LENGTH: 28 base pairs

```
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:3:

AGTGGGGGA CATCAAGCAG CCATGCAA                                        28

(2) INFORMATION FOR SEQ ID NO:4:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

CCTGCTATGT CACTTCCCCT TGGTTCTCTC                                     30

(2) INFORMATION FOR SEQ ID NO:5:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

ATAATCCACC TATCCCAGTA GGAGAAAT                                       28

(2) INFORMATION FOR SEQ ID NO:6:

(i) SEQUENCE CHARACTERISTICS:
            (A) LENGTH: 28 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:6:

TTTGGTCCTT GTCTTATGTC CAGAATGC                                       28
```